United States Patent [19]

Mirsky

[11] 4,080,448

[45] Mar. 21, 1978

[54] METHOD OF TREATING CELLULAR STRESS

[76] Inventor: Louis H. Mirsky, R.D. 2, 194 Lyonsville Rd., Boonton, N.J. 07005

[21] Appl. No.: 523,249

[22] Filed: Nov. 13, 1974

[51] Int. Cl.² .............................................. A61K 31/56
[52] U.S. Cl. .................................... 424/240; 424/242
[58] Field of Search ................................ 424/240, 242

[56] References Cited
PUBLICATIONS

Chem. Abst., vol. 57 – 7831i (1962).
Chem. Abst., vol. 74 – 1710w (1971).
Cutting's Handbook of Pharmacology, 4th Ed. (1969), pp. 396–397.
Modell, Drugs in Current Use and New Drugs, 1973, p. 37.

*Primary Examiner*—Stanley J. Friedman

[57] ABSTRACT

A method for the treatment of muscular pain and similar syndrome of body distress which are believed to be related to disruption of normal physiological activity of the body cells is described. The treatment comprises sequential intramuscular injections of from about 1 to 7 mg/cc of a sol of DOCA (desoxycorticosterone acetate in sesame oil) and intravenous injections of 100 – 1,000 mg/10cc of an aqueous solution of ascorbic acid given in a substantially simultaneous pattern of administration.

6 Claims, No Drawings

METHOD OF TREATING CELLULAR STRESS

BACKGROUND OF THE INVENTION

A large and apparently unrelated number of acute pathological conditions can produce a stress effect on the functions of the normal somatic or body cell which can only be classified as stress cell shock. This cellular shock is manifest by disruption of the normal physiological activity of the single cell. If this stress or disruption status is left untreated various types of sequellae may result depending on the severity, duration and number of single cells involved. The results of this cellular shock can result in the cell becoming nonfunctioning and necrose or die. If the patient survives this cellular condition will eventually be replaced by scar tissue. As an alternative the cell mass may recover partial function to a varying degree although this degree may not be apparent on clinical test. The recovery is almost never complete, however, and some loss almost always occurs.

The types of acute traumas which produce this cellular shock or stress can be subdivided into several broad categories to wit:

OXYGEN DEPRIVATION

This is caused by polluted air or insufficient atmospheric oxygen or insufficient cellular oxygen supply which is secondary to a physical obstruction such as blood vessel closure, anemia, pulmonary and/or cardiac disease, hemorrhage which reduces the oxygen carrying capacity to the somatic cells or other failure or defect in the oxygen transport mechanism.

TOXICITY

This is caused by the effect of blood borne soluble pollutants which block the fluid or third cellular compartment and cell membrane and hence affect oxygen utilization capacity. This may also be caused by bacterial, viral or other toxins generated by or secondary to acute infections. As a third possibility exogenous poisons or a medication overdose can cause this sequellae because of loss of the discriminatory power of the cell wall.

PHYSICAL TRAUMA

Such incidents as traumatizing wounds scalds, burns, or incisions affecting metabolic activity can produce varying degrees of local or general cellular shock.

EMOTIONAL SHOCK

This type of trauma is related to emotional reaction and is somewhat vague in its mode of activity.

At the present time inadequate means exist to treat any or all of these conditions of cellular shock noted above and a host of specific techniques have been attempted over the years in an effort to moderate or alleviate all or at least some of the aforesaid conditions. The present discovery relates to a new and heretofore unrecognized method of therapy using known therapeutic agents in a new combination and mode of administration which has been found most helpful clinically in sharply alleviating much of the manifestations of the cellular shock listed above.

DEFINITION OF TERMS

In the following description of the invention claimed several terms will be used repeatedly and it, therefore, would be useful to define several of these basic terms as follows:

1. CELL STRUCTURE

The basic physical structure of the single cell is well known histologically. It is discussed in great detail by Lawrence Ross, M.D. in CIBA SYMPOSIA, Volume 25 No. 4 printed in 1973 as so employed is intended to be so defined herein.

2. CELL FUNCTION

The various metabolic functions of the cell are well known and need not detain us here. It is, of course, known that the cell cannot function properly in the absence of an adequate concentration and purity of oxygen supply abutting and in contact with the cellular membrane. The absence of adequate oxygen upsets cellular metabolism, produces changes in the intracellular mineral concentration and content and causes the cell membrane to lose its discriminatory powers. This loss of cell function will vary with the type of cell involved with nerve cells, cardiac cells, muscular cells being specialized cells hence more rapidly subject to acute stress i.e. oxygen supply, than ectodermal cells such as hair and nails. The function described in this application relates to these biochemical and biophysical changes.

3. CELLULAR STRESS

As employed, herein, this term refers to any change in the normal content of the fluid compartment of the cell especially with reference to the oxygen content or concentration at an abnormal level so as to cause interruption of normal cellular metabolism. The cell membrane loses its discriminatory osmotic function and potassium ions flow out of the cell and are replaced by sodium ions. This causes the cell to absorb water (cellular edema) and failure to reverse this situation will cause the cell to die.

4. CELLULAR SHOCK

This term can refer to either localized shock as in cardiac or neurologic shock or generalized shock. If not relieved in the cells of a tissue or an organ the status can become irreversible causing the death of the tissue or organ or the entire body or organism. This condition is the result of failure to relieve cellular stress noted above.

It should be noted there that all prior efforts made to reverse cellular stress whether by administration of chemicals, or any means of applications of heat or cold are efforts to induce the cell to return to its normal function. Hence, it is quite obvious that any condition of acute cellular stress which interferes with the $O_2$ - $CO_2$ exchange of the cell through its cellular membranes must be quickly halted or else the cell will cease to function normally and such symptoms as pain, bizarre electrical signals on EKG, loss of muscle contractility, failure of nervous impulse conduction, halt of glomerular filtration ect. will become manifest.

In the total or aggregate this means loss of function of the organ with the relative degree of pathological change or disruption of function as well as the potential rate of and degree of recovery depending primarily on the distance of the cell from the point of trauma causing the stress. The cellular dysfunction proceeds as a geometric rather than an algebraic function and may be irregular rather than circular depending on the degree of effect on the blood supply resulting from the compression on the micro cappillaries by the surrounding edematous cells and tissue.

5. PAIN

As employed in the discussion of this invention pain is a sensory response to the structural change in the stressed cells resulting from cellular edema, wherein, the cell walls exert pressure on afferent nerve endings signalling the distress or death of the cell.

6. EDEMA — TURGOR — SWELLING

This symptom is caused by intrusion of sodium into the cell, whereby, the gross effect on a cluster of cells is a cumulative result of individual effects of cellular loss of potassium.

7. INFLAMMATION — REDNESS — RUBOR

Where employed, herein, this relates to a natural defense mechanism of the body to increase the oxygen supply to the distressed tissue by increase in the blood supply which transports the same. By a reverse action it is an attempt to remove from the cell the offending irritant and increase the cellular metabolic rate. The manifestation is generally fever or generalized increase in body heat depending upon whether the irritant is a generalized infectious irritant or local trauma or some other shock inducing agent.

BRIEF DESCRIPTION OF THE INVENTION

A therapeutic composition is described which is suitable for substantially simultaneous dual dose injection into the tissue and blood supply to the tissue of a cluster of cells or an organ suffering from acute cellular stress of the type defined herein.

As a natural corollary, thereof, a method of therapy or treatment of acute cellular stress or shock is disclosed to those skilled in the art of medicine and physiology.

The method of treatment which comprises my discovery consists of the injectable administration of the noted therapeutic agents in the manner and dosages stated:

1. sequential intramuscular injection of an injectable dose containing from 1 to about 7 milligrams of desoxycorticosterone acetate (DOCA) in a pharaceutically acceptable oily diluent such as peanut oil and simultaneously injection of.
2. an intravenous dose of an aqueous solution of from 10 – 100 milligrams/ml of ascorbic acid in amount of preferably 10 ccs of an isotonic saline solution, in a substantially sumultaneous pattern of injection.

By the terms "substantially simultaneous injection" as referred to, herein, it is meant that the two injections should be given within 10 minutes of each other or less to permit the two therapeutic agents to function at the site of the cellular stress or shock in the same therapeutic time frame.

The time of administration of the present treatment after initial onset of symptoms appears to be of the essence based on present clinical findings. The relative effectiveness of my method of treatment appears to be almost completely effective if administered within 24 hours or less from the onset of symptoms. The degree of effect is rapidly reduced, thereafter, so that after a lapse of 3 to 5 days depending on the patient and the particular cellular stress treated the treatment will not be effective. This loss of therapeutic effect is believed due to the spread of micro-capillary thrombosis of the stressed cell blood supply and circulation or simply to the fact that the stress shocked cell has reached the point of "no return" or some similar reason not entirely known to the inventor.

Furthermore, increase of dosage or repetition of treatment within 48 hours from the time of initial treatment in the manner indicated above does not show a therapeutic effect. The treatment is either effective on initial administration within the dose limits specified or not effective. Whether or not the treatment is effective will be manifest to the patient and his physician generally within 30 to 40 minutes after the administration of the last injection. It has not been found to work in diabetic patients.

In general it is preferred to administer the DOCA intramuscularly first followed immediately by the intravenous administration of the ascorbic acid but the order may be reversed so long as the time span between injections is respected and maintained within the limits indicated.

No adverse effects of any kind were noted in the several clinical applications of the method of treatment as further elaborated in case histories, herein, below. Where the proper therapeutic conditions, as noted above, were maintained there was no reoccurence of the condition treated over a protracted period of many months time.

There were no changes in the vital signs noted in any of the patients treated and no "drug reactions" noted. The blood pressure of hypersensitive patients was not affected.

Although DOCA is available commercially as both an oily liquid and an aqueous suspension the latter may not be used to treat cellular stress and cell shock because for some unknown reason it does not work clinically due to a biochemical mechanism as yet unexplained. Likewise oral administration of either or both ingredients does not appear to work because of the time lag to get the therapeutic agents to the site of the cellular distress at substantially the same time. If the ascorbic acid must be ingested orally and assimilated from the gut it will arrive at the treatment areas long after the intramuscular dose of DOCA has dissipated from the therapeutic site.

Still another parameter to my method of therapy is that the DOCA must be administered intramuscularly and not orally intravenously or intraperitoneally. In the first case the drug will reach the reaction or therapy site too late to be effective if administered orally and forced to find its way into the distressed tissue via the blood supply.

Likewise if administered intravenously it can cause an embolism in the blood stream or if administered intraperitoneally it can act as a foreign body and cause peritonitis. To be effective it must be administered into the body fluid which surrounds and bathes the cells of the tissue which are under stress. It can find its own way into the cell through the cell membrane and await the arrival of the ascobic acid if injected into the tissue of the organ or muscle itself.

The general effectiveness of the composition of the invention is quite widespread especially in the treatment of orthopedic conditions and related neurological effects. In addition to this treatment of cellular stress in cerebral vascular edema pressure cases is noted, hereinbelow, as is treatment of cellular edema arising from or as an aftermath of general or neurosurgery. A particular area of therapy is shown with respect to the treatment of the headache which frequently follows the administration of spinal anesthesia, which is commonly referred to as "post-spinal headache."

The following examples will illustrate the widespread clinical success achieved by the therapeutic composition of the invention. The dose administered by injection in all of the following cases was maintained at 5 milligrams of D.O.C.A. in 1 milliliter of peanut oil. The ascorbic acid dose was 1000 milligrams in a 10cc aqueous solution administered intravenously from a vial of the same. This will be referred to in the following examples as the therapeutic dose or "T.D.".

CLINICAL EXAMPLE 1

Treatment of Orthopedic Conditions

R.N. — a 40 year old female presented with a first attack of lumbo-sacral sprain, cause undetermined. She stated that she bent down to pick up something and felt a pain in her back. On examination, there was acute lumbo-sacral muscle spasm, the spinal column was S shaped and the left shoulder was about 2 inches lateral to the pelvis. The T.D. was administered and within ½ hour, the patient left the office relieved of pain. In other cases, it was noted that the degree of relief depended on the therapeutic criteria noted above.

No reoccurrence of symptoms or disability in those case of "initial occurrence" was observed over a lengthy period of time. I.e., several months. The above result was confirmed in approximately 100 other lumbar and lumbo-sacral sprains cases over a period of months as well cervical sprain cases.

CLINICAL EXAMPLE 2

S.G. — age 35, florid male, hypoglycemic, presented himself at the office in great pain with an acute subdeltoid bursitis with the usual total limitation of motion. The T.D. was administered and the patient had almost total relief within ½ hour while waiting in the office. No further medication was given although the patient complained of a slight residual ache, which had disappeared by the next morning. There was no reocurrence over an extended period of time.

CLINICAL EXAMPLE 3

H.D. — This patient, age approximately 50 years, presented with pain and immobility in that he was unable to abduct his left arm because of an acute tendonitis of the supraspinatus tendon traversing the bicipital groove of the humeral head. He gave a history of having played baseball with his son the day before and that the disability occurred during the night. X-rays revealed a calcified tendonitis. Upon telephone consultation, an orthopedic specialist advised either expectant treatment or surgery to remove the calcification around the tendon. He also stated that the cure rate was approximately 50%. Although the patient was known to be extremely allergic to a great variety of allergens and was also an asthmatic. The T.D. was administered and within 30 minutes the patient was completely relieved with no recurrence.

Neurological and Neurosurgical Conditions.

CLINICAL EXAMPLE 4

Facial Paralysis (Bell's Palsy)

R.E. — female, approximately 40 years old, presented with a typical left-sided Bell's Palsy. Although the condition was more than 24 hours old, the T.D. was administered and she experienced total relief except that when she encountered periods of stress, she would feel a nervous tingling. This residual was treated by other means.

CLINICAL EXAMPLE 5

Q.M. — this female in her late 20's was seen by me at her home. She was not my patient but was see "on call" for another physician. She had a typical left-sided Bell's Palsy occurring. The T.D. was immediately administered and she got immediate and total relief within ½ hour. To my knowledge, there was no recurrence over a period of time. No futher therapy was given.

Approximately 30 other similar cases were treated with comparable good result.

STROKE (CEREBRAL VASCULAR ACCIDENT) (C.V.A.)

CLINICAL EXAMPLE 6

A.D. — a female, about 69 years old, hypertensive, who had undergone much surgery including gall bladder surgery, intenstinal surgery, etc. years previously. I was called to her home as an emergency be her daughter who was an RN nursing supervisor. The woman was a typical acute C.V.A., which had just occurred and as was certified by her daughter. She had paralysis of the left arm, left leg, was unable to speak and her tongue extruded to the left. The T.D. was immediately administered and she recovered completely with no residuals and was up and about the following morning. The patient was seen over an extended period of time. She did not have any further strokes and she eventually died several years later of senility and cerebral vascular insufficiency.

Three cases were treated with total or maximal relief. There were no recurrences or excessive disability.

In cases of stroke, they either die or recover. The amount of disability depends on the number of brain cells immediately destroyed by the hemorrghic occurrence. However, the previously stated "ground zero" effect must be taken into account since many cells die as a result of edematous pressure. If this can be relieved, then the disability will only be affected by the number of cells immediately destroyed.

ANESTHESIOLOGY

Post Spinal Annesthesia Headache — this is a not uncommon condition following spinal anesthesia. The headache can be devided into two types, the most common one which is the immediate spinal headache and which occurs within 12 to 24 hours after administration. The delayed type occurs approximately five days later.

There were many discussions as to the cause of post-spinal headache. These included differences in spinal needle size, mode of administration, etc. Some of the post-spinal complications include paralysis of a leg, paresthesias and others. Therapy for post-spinal headaches is also variable. In view of the fact that there was such divergence of opinion as to causation and since I was on the hospital anesthesiology staff in charge of my own service, I felt that none of these reasons as to cause were entirely true. I felt that the reaction occurred primarily at the spinal fluid-producing cells at the base of the 4th ventricle. I therefore, decided to keep statistics on the type of anesthesia, the person who administered the spinal and the size of needle, etc. In a series of 30 cases of post-spinal headaches, none of the above factors appeared to be related as a cause of the headache. At the same time, I also instructed the surgical residents to notify me immediately by telephone upon the occurrence of a post-spinal headache. In all of these cases, immediately upon notification, I administered the T.D. and relief was obtained by all the patients. I administered the T.D. and relief was obtained by all the patients.

CLINICAL EXAMPLE 7

R.F., female, age 48, who had a hysterectomy performed under spinal anesthesia on the previous day. When seen by me, at approximately noon, she was half sitting in bed with severe headache, groaning and in great discomfort. The resident administered the T.D. under my supervision. During this procedure, a tray lunch was served to the patient. Almost immediately after the administration of the T.D., the patient sat up in bed and devoured her lunch. There was no recurrence of the headache.

MEDICAL CONDITIONS

It has never been definitely established as to the cause of myocardial infarction. I have always felt that an acute myocardial infarction was secondary to electro-bio-chemical changes in the third compartment of the heart muscle cells, creating a condition of cell shock, destruction of cell activity and metabolism, in most cases, a limited area of cell death due to lack of oxygen supply and this "ground zero" area affects the surrounding myocardial cells by reason of emema cutting off circulation via microcapillary thrombosis. The status of chlolesterol has not been definitely settled. I feel that basically, the cholesterol deposits in the coronary arteries serve only to cut down the blood supply and, therefore, the amount of oxygen feeding the myocardial cells. Any form of acute stress will, therefore, shortly precipitate an acute myocardial infarction. Furthermore, the extension of the acute myocardial infarction usually occurs three to five days after the initial attack. I, therefore, feel that the use of the T.D. will not only limit the area of infarction but will prevent extension and later on angina pectoris.

CLINICAL EXAMPLE 8

Three patients with acute myocardial infarction were treated at home because no bed was available in a private hospital and they refused to go to a city hospital. All three were males approximately 50 years old. They were seen at home on an emergency basis. The T.D. was administered, the precordial pain stopped, there were no M.I. fibrillation visible on EKG, the patients were out of bed and sitting up the following day. There were no sequellae. Over an extended period of time, these patients had no recurrence of an acute M.I.

ACUTE NEPHROSIS

Two patients, both females, were seen with an acute nephrosis following virus infection. One patient of approximately 35 years old was admitted to the hospital where she was seen in consultation with medical specialists. She had complete anuria and the surgeons decided to do a kidney stripping operation. (Decortication). This was done the following day. The patient died shortly in a state of complete anuria.

The second case was seen at home and the T.D. was administered by me. Shortly, thereafter, her anuria was resolved, she started secreting urine. There were no sequellae or complications.

In Respiratory Distress Syndrome 70% of patients with major thoracic trauma suffer a 60 to 80% fatality rate. There is progressive pulmonary consolidation. Rib fracture or contusion of the chest muscles is not necessary. In this blunt trauma to the chest, the patient can also suffer a myocardial contusion in which EKG changes are similar to a myocardial infarction.

other conditions in which the T.D. may give relief and which should be considered are (1) Snake bite — there is generalized toxicity with neurologic and renal degeneration.

(2) Myoglobinemia and Myoglobinurea — in this condition, which is usually due to blunt trauma, there is breakdown of the muscle cells secondary to cell shock. The cell components are released into the general circulation and this produces the pathologic status. Unless the muscle blood supply is grossly comprised, there will not be any permanent muscle degeneration.

The T.D. should also be utilized in such conditions as acute asthma, other severe allergic manifestations, acute rheumatic fever.

The following is a specific embodiment of the preferred mode of administration of the therapeutic composition used in the preceding clinical examples:

(a) A tourniquet is placed around the upper arm of the patient in a routine manner and 1cc (5mg of D.O.C.A.) in an oil carrier such as sesame oil or peanut oil is injected intramuscularly into the Deltoid muscle above the torniquest using a 2cc syringe and a 22 gauge 1¼ inch needle.

(b) The tourniquet is released immediately, thereafter, and the Vitamin C in aqueous solution is then intravenously injected into the general circulation by injection into the same arm. The quantity of Vitamin injected has been about 1,000 milligrams from a 10cc vial in aqueous solution but this can be varied somewhat.

The therapeutic composition of the invention has a very wide range of application. In the several preceding examples some instances are cited where the treatment was clinically applied and found to be effective in treating certain types of symptoms caused by acute cellular stress or shock. However, there are conditions which directly parallel the first group of cases actually treated and in these areas the treatment will be probably effective. A third class of conditions exist where the treatment may be effective but further actual experimentation is required to verify the belief.

Of the cases treated, the patient would normally appear at the clinic with pain muscle spasms, loss of motion of his arm or leg or other portions of his anatomy. The causes for such symptons were various auto and home accidents, falls, a variety of reasons pecular to this type of stress or strain situation of frequently unknown etrology. Acute episodes of chronic back were also frequently encountered among the 100 or so cases treated.

In the area of probably effective uses of my therapeutic composition is useful in the reduction of swelling prior to manipulation of fractures and dislocations. In various forms of traumatic myositis caused by direct trauma it can be used. Of course in the treatment of acute subdeltoid bursitis and acute tendonitis it has been successfully employed in about 30 cases. Notably, whether the bursa was calcified or not as demonstrated by X-Rays was not a factor affecting relief of the acute condition. There were no recurrences over an extended period of time.

The treatment is probably effective also in other acute neuridities and neurology such as trigeminal neuralgia, sciatica, tic doloreux and Menieres Diesease. It may also be useful in the treatment of polio since the trauma of cellular stress and swelling is related to this condition.

The present therapy to reduce brain or spinal cord edema is well known and only partially effective and much residual disability is encountered due to the death of nerve cells surrounding the "ground zero" where the trauma due to surgery or accident occurred. The use of the present therapy to alleviate this edema and, therefore, much of the permanent disability connected, therewith, is suggested by my present knowledge of its beneficial attributes.

In abdominal surgery where wound dehiscence is a frequently encountered condition the therapeutic composition would appear benefical. The alleviation of redness, swelling, tenderness of the tissue and pain all are conditions which respond to application of the method of treatment disclosed herein.

Generalized shock following a traumatizing accident should respond to the treatment described. Burns and scalds result in immediate death to the body cell layers which are literally "cooked". Below these layers the cells are thrown into a state of cellular shock and become edematus with massive fluid loss. The reversal of these conditions of the still viable cells is within the ambit of this present discovery. In stress ulcers and organ transplant situations where cellular shock is involved the new method treatment is suggested because the essential mode of stress of cells is in these cases as well as the others also manifest.

As a general statement the method of therapy spelled out, herein, is applicable in all cases where acute traumatic cell shock altering the bio-electrical-chemical status of the 3rd fluid compartment or cell is a possible factor in oxygen delivery or oxygn utilization is a problem.

In the case of post spinal anesthesia headache the same can be immediate to occur within 12 to 24 after administration of the spinal anesthetic, or delayed until about 5 days after spinal anesthetic. As noted above, my ethod of treatment was found useful in all of the spinal headache patients in which it was tried in a series of at least 30 cases regardless of the cause of the headache or if in fact the cause was ascertainable at all.

Although the invention has been described using a particular corticosteriod it should be understood that the concept of the invention is broad enough to encompass other steriods which are well known corticoids and may be considered as equivalents to the desoxycorticosterone acetate described in the several examples set out hereinabove. Such well known glucocorticoids as ARISTOCORT, CELESTONE, CORTEF, DECADRON, METICORTELONE, AND PRESNISONE to name a few of the tradenames of popular corticoids of commerce would be expected to perform in a similar fashion to the specific corticoid which I used in my clinical evaluation of my method of treatment. The dosage for such ingredients roughly be about the same and all of these materials are commerically available.

The following several claims will more specifically point out the invention described in this specification.

I claim as my invention:

1. A method for the alleviation of acute somatic cellular stress in mammels including humans which comprises the substantially simultaneous and sequential injectable administration to man of a combination of a therapeutically effective amount from 1 to 7 milligrams of a corticosteroid in a non toxic oleagenous carrier and a therapeutically effective amount of from 100 to 1,000 milligrams of an aqueous solution of ascorbic acid, the corticosteroid being first injected intramuscularly and the ascorbic acid being injected intravenously.

2. According to claim 1 a method for the alleviation of acute cellular stress which comprises the substantially simultaneous and sequential injectable administration of a combination of a therapeutically effective amount of from 1 to 7 milligrams of desoxycorticosterone acetate in a non toxic oleagenous carrier and a therapeutically effective amount of from 100 to 1,000 milligrams of an aqueous solution of ascorbic acid, the desoxycorticosterone acetate being injected intramuscularly first and the ascorbic acid being injected intravenously.

3. According to claim 2 a method for the alleviation of acute cellular stress which comprises the substantially simultaneous and sequential injectable administration to man of a combination of at least 1 milligram of desoxycorticosterone acetate and at least 100 milligrams of an aqueous solution of ascorbic acid, the desoxycorticosterone acetate being first injected intramuscularly and the ascorbic acid being injected intravenously.

4. A method according to claim 1, wherein, the desoxycorticosterone is injected in amount of from 1 to 7 milligrams per milliliter and ascorbic acid is injected in amounts of 10 to 50 milligrams per milliliter.

5. A method according to claim 1, wherein, the desoxycorticosterone acetate is injected intramuscularly in a dose of 5 milligrams per milliliter of liquid and the ascorbic acid being injected intravenously in a dose of 100 milligrams per milliliter.

6. A method according to claim 1, wherein, the desoxycorticosterone acetate component is injected first and within 10 minutes thereafter the ascorbic acid component is injected.

* * * * *